United States Patent [19]

von der Decken

[11] Patent Number: 5,336,201
[45] Date of Patent: Aug. 9, 1994

[54] SYRINGE DRIVING APPARATUS

[75] Inventor: Claus von der Decken, Aichach, Fed. Rep. of Germany

[73] Assignee: Baxter International Inc., Deerfield, Ill.

[21] Appl. No.: 906,087

[22] Filed: Jun. 29, 1992

[51] Int. Cl.$^5$ ............................................. A61M 5/315
[52] U.S. Cl. ................................... 604/223; 604/228; 128/DIG. 12
[58] Field of Search .............. 604/181, 218, 223, 228, 604/233, 97; 128/DIG. 12; 222/327; 417/443, 464, 469, 481

[56] References Cited

U.S. PATENT DOCUMENTS

| | | | |
|---|---|---|---|
| 2,074,401 | 3/1937 | Kauzal | 604/223 |
| 2,164,711 | 7/1939 | Kadavy . | |
| 2,200,012 | 5/1940 | Russell et al. | 417/464 |
| 3,819,091 | 6/1974 | Hollender | 604/223 |
| 3,822,700 | 7/1974 | Pennington . | |
| 3,861,388 | 1/1975 | Vaughn | 604/86 |
| 3,905,365 | 9/1975 | Colombo | 604/223 |
| 4,033,346 | 7/1977 | Phillips et al. | 604/223 |
| 4,084,606 | 4/1978 | Mittleman . | |
| 4,132,231 | 1/1979 | Puccio | 128/DIG. 12 |
| 4,168,701 | 9/1979 | Chiulli | 604/181 |
| 4,204,539 | 5/1980 | Van Brugge . | |
| 4,253,501 | 3/1981 | Ogle . | |
| 4,262,671 | 4/1981 | Kersten . | |
| 4,316,558 | 2/1982 | Kubiak | 222/181 |
| 4,576,594 | 3/1986 | Greenland . | |
| 4,623,343 | 11/1986 | Thompson . | |
| 4,737,151 | 4/1988 | Clement et al. | 604/223 |
| 4,769,008 | 9/1988 | Hessel . | |
| 4,779,997 | 10/1988 | Schmidt . | |
| 4,808,165 | 2/1989 | Carr | 604/97 |

FOREIGN PATENT DOCUMENTS

| | | | |
|---|---|---|---|
| 0224201 | 11/1924 | United Kingdom | 417/464 |
| 0354573 | 8/1931 | United Kingdom | 417/464 |
| 0580308 | 9/1946 | United Kingdom | 417/464 |

OTHER PUBLICATIONS

Block Medical, Homepump TM Circular.

*Primary Examiner*—C. Fred Rosenbaum
*Assistant Examiner*—Frank Wilkens
*Attorney, Agent, or Firm*—Paul E. Schaafsma; Paul C. Flattery

[57] ABSTRACT

An apparatus 10 for driving a plunger 134 of a syringe 16 includes a plate 48 on the top 38 of a frame 36 and a structure 62 on the plate 48 for releasably attaching the cylinder 130 of the syringe 16 to the frame 36 and securing the cylinder 130 against lengthwise movement relative to the frame 36. A lever 76 is pivotably attached to the top 38 of the frame 36 a selected distance from the plate 48. A pair of pivot pins 108,110 releasably pivotably attach the distal end 150 of the plunger 134 of the syringe 16 to the lever 76. In this manner, pivotable movement of the lever 76 is translated into lengthwise movement of the plunger 134. An apparatus 10 for transferring a measured amount of fluid from a first fluid supply 14 to a fluid reservoir 170 includes a syringe 16, the syringe driving apparatus 12 and a two-way check valve 18. The fluid supply 14, the fluid reservoir 70 and the syringe 16 are maintained in fluid communication through the two-way check valve 18.

28 Claims, 3 Drawing Sheets

SYRINGE DRIVING APPARATUS

BACKGROUND OF THE INVENTION

The present invention is directed toward an apparatus for conveying a fluid between two reservoirs and, more particularly, toward a fluid transfer apparatus utilizing a syringe and a syringe driving apparatus for transferring a measured amount of fluid from a fluid supply to a fluid reservoir.

BACKGROUND ART

In recent years, spiralling hospital costs and shortages of critical facilities have led to efforts to promote outpatient treatment. Certain treatments require administration of small doses of medication over extended periods of time. For example, infusion of some antibiotic and chemotherapy medications. The healthcare industry has addressed the need to provide such medications outside of the clinical environment by developing a variety of infusion pumps for delivering medication to patients that are ambulatory or receiving home care.

One highly successful low-cost ambulatory infusion system utilizes a disposable elastomeric ambulatory infusion pump having an elastomeric bladder defining a therapeutic fluid reservoir. Elastomeric strain on the elastomeric bladder tends to collapse the reservoir, thereby providing a positive pressure on the therapeutic fluid within the bladder. A fluid outlet is provided with a flow regulator for delivering a constant predetermined flow of therapeutic fluid from the reservoir to a patient through a hypodermic needle.

The elastomeric bladder of such an elastomeric ambulatory infusion pump is usually filled with a therapeutic fluid from a fluid supply through the use of an intermediary device such as a disposable 50 ml syringe. Typically, the filling process involves connecting the syringe to an outlet of a therapeutic fluid supply, withdrawing the plunger of the syringe to draw a selected volume of the therapeutic fluid into the syringe, disconnecting the syringe from the fluid supply, connecting the syringe to the elastomeric ambulatory infusion pump and pushing the plunger of the syringe forwardly to discharge the selected volume of therapeutic fluid into the elastomeric bladder. When the amount of fluid to be conveyed to the elastomeric bladder exceeds the volume of the syringe, this process must be repeated until the bladder is filled with the desired volume. Where multiple elastomeric ambulatory infusion pumps are to be loaded with therapeutic fluid, this process must be repeated with each pump.

In some countries, such as France, the national healthcare system requires that nurses mix and administer each dosage of medication. Thus, the elastomeric ambulatory infusion pump must be individually filled, often at the location of the patient, before administration to the patient. In other countries, such as the United States, the home care practice is to provide the patient with several weeks' supply of premeasured dosages that can be self-administered. Thus, pharmacists often must fill a number of elastomeric ambulatory infusion pumps for their customers. Filling an elastomeric ambulatory infusion pump with several volumes of a syringe can be awkward, time-consuming and fatiguing, and these problems are exacerbated when numerous pumps must be so filled. It is therefore readily apparent that a device for loading elastomeric ambulatory infusion pumps which does not require repeated connections and disconnections to provide a selected amount of fluid, which provides a mechanical advantage and which is compact and readily transportable is highly desirable.

The prior art has developed a variety of high speed automated filling devices which can be used to convey therapeutic fluids from a fluid supply to an elastomeric ambulatory infusion pump. However, these devices typically required connection to an electrical supply, so they may not be suitable for field use. In addition, these devices are typically heavy, bulky and fragile, making them unsuitable for transport. Finally, these devices typically require cleansing and sometimes sterilization of the pumping mechanism when different therapeutic fluids are conveyed therethrough.

One attempt to address the shortfalls of these automated filling devices uses a disposable 50 ml syringe of the type typically used to fill infusion pumps. The cylinder of the syringe is fixedly mounted to a slidable carriage in a vertical alignment. The carriage rides on a pair of vertical rails extending from the base of the device. A clamp is provided on the base for securing the distal end of the plunger to the base of the device between the rails. A pair of arms is pivotably mounted to a pair of rods behind the slidable carriage and extend forwardly therefrom. Each arm engages a bracket on the slidable carriage. Pivotal movement up and down of the arms causes corresponding up and down sliding of the slidable carriage and thus movement of the cylinder up and down relative to the fixed plunger. By moving the arms upward, fluid is drawn into the syringe and by moving the arms downward, fluid is expelled from the syringe and into an elastomeric ambulatory infusion pump in fluid communication with the syringe outlet.

While this device provides certain advantages over automated filling devices, notably its relatively simple structure, its use of a disposable syringe and the fact that it does not require electricity to operate, it still has several problems. Most significantly, it has a number of mechanical linkages which are subject to failure with repeated usage. In addition, the syringe cylinder must be fastened to the slidable carriage by the use of a pair of thumb screws, making it relatively time-consuming and difficult to attach the syringe to the carriage. The plunger must also be screwed to the base of the structure, further complicating the process of loading a syringe to the device. Finally, because the structure requires vertical orientation of the syringe, it is bulky and therefore cumbersome to transport and store.

The present invention is directed toward overcoming one or more of the problems discussed above.

SUMMARY OF THE INVENTION

An apparatus for driving a plunger of a syringe includes a frame having a top and a bottom. A bracket is provided on the frame for releasably attaching a cylinder of a syringe to the frame and securing the cylinder against lengthwise movement relative to the frame. A lever is pivotably attached to the top of the frame a selected distance from the bracket. A bracket on the lever is provided for releasably pivotably attaching a distal end of a plunger of a syringe to the lever. Upon attachment of a syringe to the syringe driving apparatus, pivotable movement of the lever is translated into movement of the plunger.

The syringe may include a nozzle defining a port extending forward from a front wall of its cylinder. In this instance, the first bracket includes a plate on the frame fixed against lengthwise movement relative to the frame and a structure on the plate for releasably attaching the nozzle to the plate. This structure may be a tongue on one of the plate and the nozzle and a cooperating groove on the other of the plate and the nozzle. The plate is preferably mounted to the top of the frame so that it pivots about a line perpendicular to a longitudinal axis of a syringe attached to the frame. The bracket on the lever for releasably attaching the distal end of a plunger to the lever may be a pin on the lever, the pin being receivable in a pin receiving groove at the distal end of the plunger. The driving apparatus may further include at least one suction cup on the bottom of the frame for attaching the driving apparatus to a fixture.

In a highly preferred embodiment, the lever of the driving apparatus includes a handle extending lengthwise from beyond the removable, pivotable attaching bracket for providing a mechanical advantage decreasing the amount of force necessary to drive a plunger of a syringe forward and rearward within a cylinder of the syringe. Preferably, the plate has a top edge with an arcuate tongue therein for receiving a groove on a cylinder of a syringe, the arcuate tongue further being configured to receive the handle so that when a syringe is not attached to the driving apparatus, the lever can be pivoted substantially parallel to and onto the frame with the lever handle received in the arcuate tongue for compact storage of the driving apparatus.

Another aspect of the present invention is an apparatus for transferring a measured amount of fluid from a first fluid supply to a fluid reservoir including a syringe in combination with the above-described driving apparatus. A two-way check valve may be provided in fluid communication with a port on the syringe, the fluid supply and the fluid reservoir. The two-way check valve permits a flow of fluid (A) from the fluid supply through the port and into a cylinder of the syringe as a piston of the syringe moves rearward in the cylinder and (B) from the cylinder and into the fluid reservoir as the piston moves forward in the cylinder. The fluid reservoir may be an elastomeric ambulatory infusion pump.

The apparatus for driving a plunger of a syringe of the present invention provides a compact, lightweight structure for translating pivotable movement of a lever to forward and rearward movement of a plunger in a syringe for ease in drawing a fluid into and discharging a fluid from a syringe. The driving apparatus is lightweight and compact for ease of storage and transportation. In addition, a syringe may be readily attached and removed from the driving apparatus. Moreover, the apparatus provides a structure for attaching it to a fixture to thereby further facilitate ease in driving a syringe. The syringe driving apparatus in combination with a syringe and a two-way check valve provides an inexpensive device for quickly and easily transferring therapeutic fluid from a therapeutic fluid supply to an elastomeric ambulatory infusion pump. Use of this combination eliminates the need of repeatedly attaching a syringe to the therapeutic fluid supply and then to the elastomeric ambulatory infusion pump inlet to fill the elastomeric bladder to a selected volume in excess of the syringe's volume.

DETAILED DESCRIPTION OF THE PREFERRED EMBODIMENT

Figure 1:
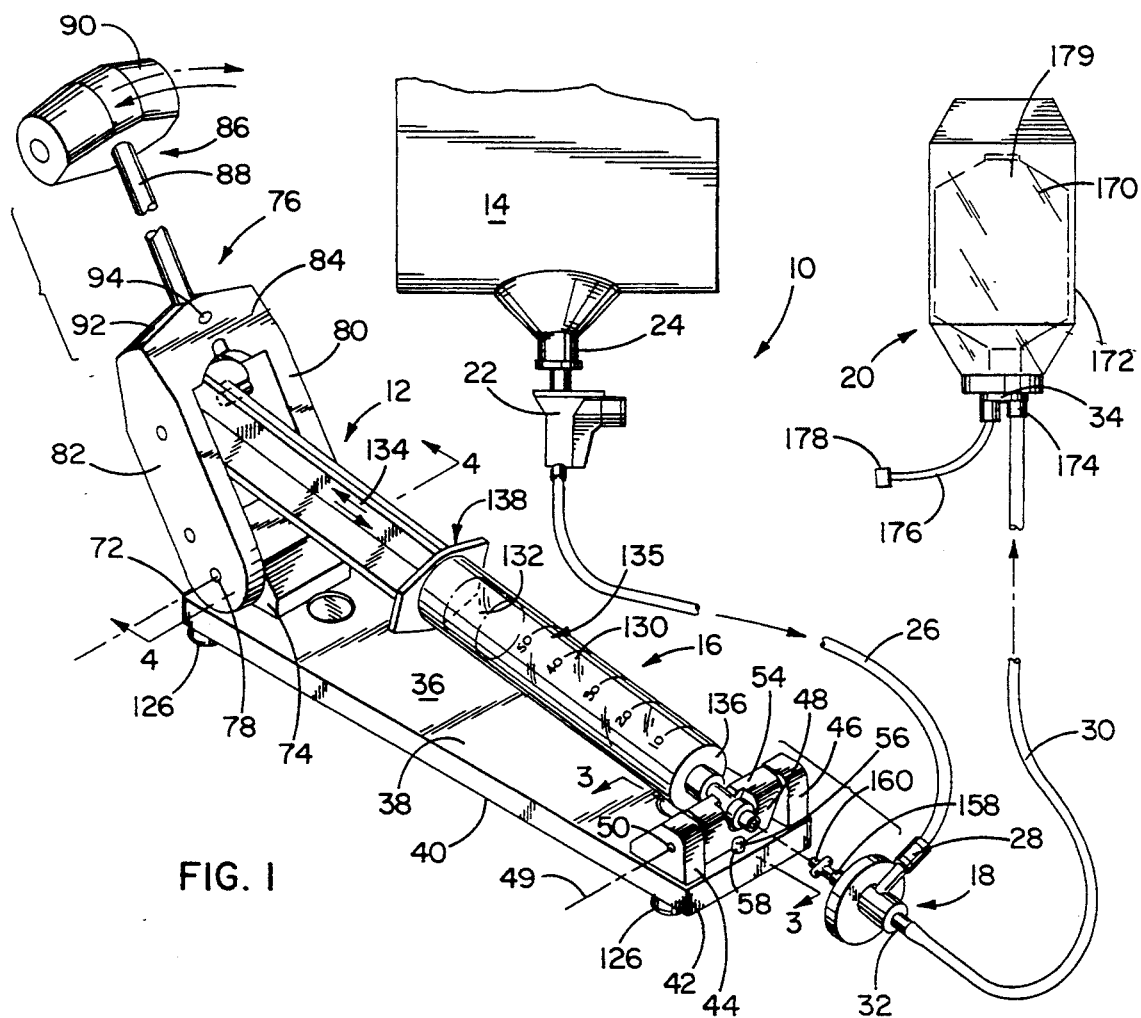
FIG. 1 is a perspective view of an apparatus for transferring a measured amount of fluid from a first fluid supply to a fluid reservoir in accordance with the present invention, including the levered syringe driving apparatus of the present invention.

An apparatus 10 for transferring a measured amount of fluid from a first fluid supply to a fluid reservoir in accordance with the present invention is illustrated in FIG. 1. The fluid transfer apparatus 10 includes a syringe driving apparatus 12, a therapeutic fluid supply 14, a syringe 16, a two-way check valve 18 and an elastomeric ambulatory infusion pump 20. A vented spike 22 is illustrated in fluid communication with a portal 24 of the therapeutic fluid supply 14. A flexible conduit such as a first piece of polyvinyl chloride (PVC) tubing 26 maintains fluid communication between the vented spike 22 and an inlet port 28 of the two-way check valve 18. A second piece of PVC tubing 30 maintains fluid communication between an outlet port 32 of the two-way check valve 18 and an inlet 34 of the ambulatory infusion pump 20.

Figure 2:
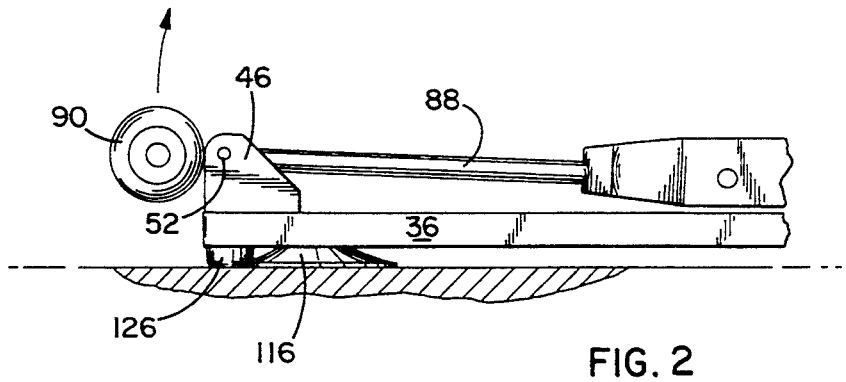
FIG. 2 is a fragmentary side elevational view of the front portion of the syringe driving apparatus of the present invention.
Figure 5:
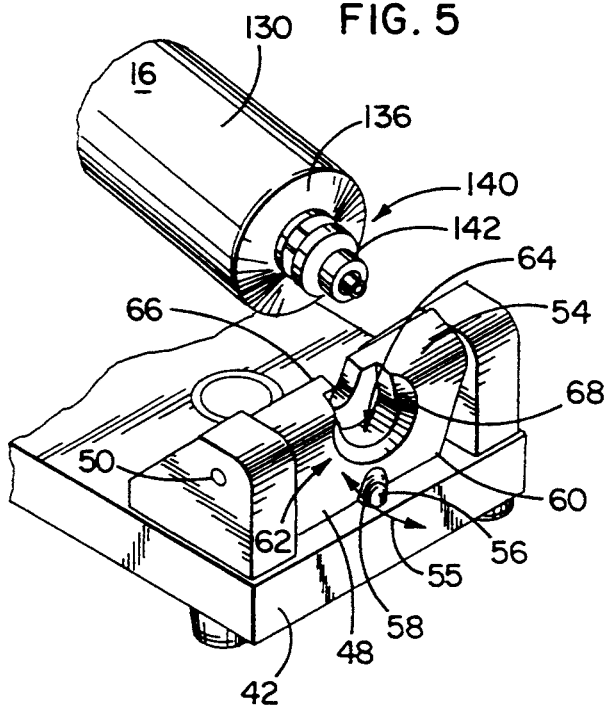
FIG. 5 is a fragmentary perspective view of the structure for releasably attaching a cylinder of a syringe to the syringe driving apparatus of the present invention.

The syringe driving apparatus 12 has a base or frame 36 having a top 38 and a bottom 40. At the front 42 of the base 36 are a pair of spaced apart first and second studs 44,46. A plate 48 is pivotably mounted between the first and second studs 44,46 by a first hinge pin 50 and a second hinge pin 52 (see FIG. 2) for pivoting about an axis 49. As best illustrated in FIG. 5, the plate 48 is mounted between the first and second studs 44,46 by the first and second hinge pins 50,52 proximate the top 54 of the plate 48 so that the plate 48 is pivotable as illustrated by the arrow 55 about an axis transverse to the length of the base 36. A stop 56 protrudes from the top 38 of the base 36 and is received within a divot 58 at the bottom 60 of the plate 48 to halt forward pivoting of the plate 48.

Again with reference to FIG. 5, a stepped arcuate groove 62 is cut into the top 54 of the plate 48 and extends therethrough. The stepped arcuate groove 62 has an arcuate tongue 64 towards the back 66 of the plate 48. A beveled surface 68 is between the arcuate groove 62 and the front 70 of the plate 48. In a like manner, a beveled surface (not shown) is between the back 66 of the plate 48 and the arcuate tongue 64.

Figure 4:
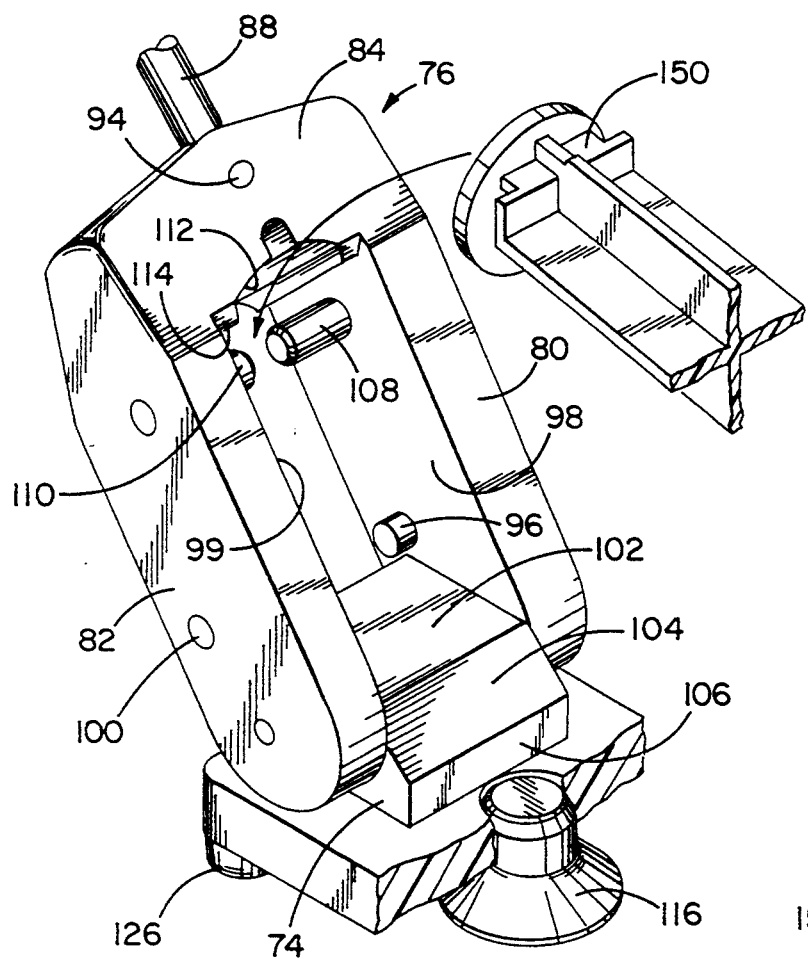
FIG. 4 is a fragmentary view of the lever of the syringe driving apparatus and plunger for engagement therewith of the present invention.

Proximate the rear 72 of the base 36 is a pedestal 74. A lever 76 is pivotably mounted to the pedestal 74 by a third hinge pin 78 and a fourth hinge pin 79 (see FIG. 8). More particularly, the lever 76 includes a pair of spaced apart legs 80,82 joined by a bridge 84. A handle 86 including a bar 88 and a grip 90 extends from the top 92 of the bridge 84. The bar 88 is joined to the bridge 84 by a screw 94, but of course may be joined by an adhesive or any other fastener. The first and second legs 80,82 straddle the pedestal 74 and are pivotably mounted thereto by the third and fourth hinge pins 78,79 to pivot about the axis 95 parallel to the axis 49. As best seen in FIG. 4, the first leg 80 has a bumper 96 on its inner surface 98. A similar bumper 100 extends from the inner surface 99 of the second leg 82. The bumpers 96,100 engage the top 102 of the pedestal 74 to halt rearward pivoting of the lever 76 in a loading position illustrated in FIG. 1. A beveled surface 104 is provided between the top 102 and the front 106 of the pedestal 74 to provide clearance for the bumpers 96,100 when the lever 76 is pivoted forward. Proximate the bridge 84 and extending inwardly from the inner surface 98 of the first leg 80 and the inner surface 99 of the second leg 82 are first and second pivot pins 108,110. An arcuate groove 112 is cut in the bottom 114 of the bridge 84.

Figure 8:
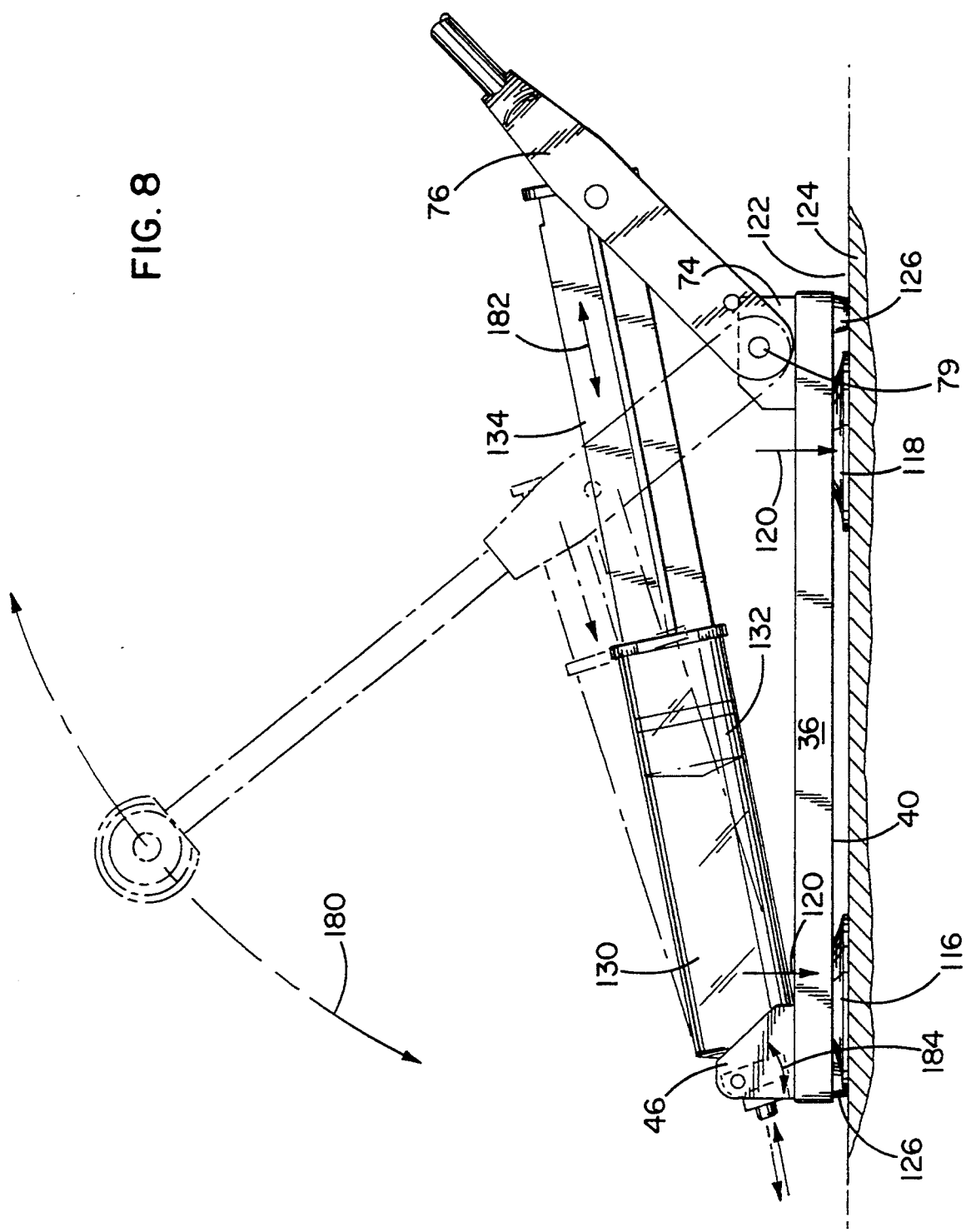
FIG. 8 is a side elevational view illustrating the operation of the syringe driving apparatus of the present invention.

As best seen with reference to FIGS. 4 and 8, first and second suction cups 116,118 extend from the bottom 40 of the base 36. Upon application of a downward force indicated by the arrows 120 upon the first and second suction cups 116,118, the suction cups adhere to a nonporous surface 122 of a fixture 124 to fix the syringe driving apparatus 12 against movement relative to the fixture 124. A silicone bearing 126 extends from each corner of the bottom 40 of the base 36 for laterally stabilizing the syringe driving apparatus 12.

The syringe driving apparatus can be made from many materials. Preferably the base 36 and arms 80,82 and bridge 84 of the lever 76 are made of a rigid plastic. The bar 86 is metal and the grip 90 is made of plastic.

The syringe 16 includes a cylinder 130 having an elastomeric piston 132 disposed therein for axial movement longitudinally of the cylinder 130 under a driving force applied to the plunger 134 attached thereto. The cylinder 130 has graduated indicia 135 for indicating the volume of fluid within the syringe 16. The cylinder and plunger are injection molded from any suitable thermoplastic.

Figure 7:
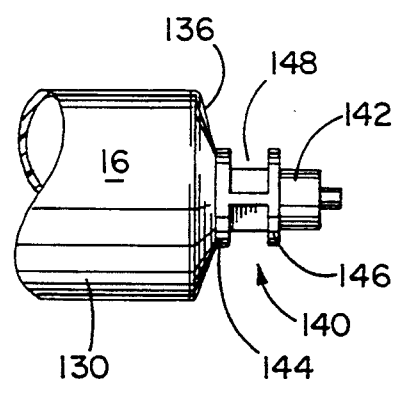
FIG. 7 is a fragmentary side elevational view of the outlet port of a preferred embodiment of a syringe for use with the present invention.

The cylinder 130 has a front wall 136 and an open back end 138. As is clearly seen in FIGS. 1 and 8, the plunger 134 extends rearwardly out of and from the cylinder 130 through the open back end 138. As best seen in FIGS. 5 and 7, a port 140 extends from the front wall 136 of the cylinder 130 of the syringe 16. A male luer connector 142 is provided at the front of the port 140 for connection to a standard female luer connector. An annular shoulder 144 proximate the front wall 136 of the cylinder 130 and an annular collar 146 spaced axially therefrom define an annular recess 148 on the port 140.

Figure 6:
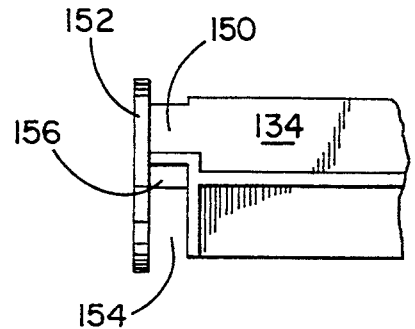
FIG. 6 is a fragmentary side elevational view of a preferred embodiment of the distal end of a syringe plunger for use with the syringe driving apparatus of the present invention.

With reference to FIGS. 4 and 6, it can be seen that the distal end 150 of the plunger 134 has a circular cap 152 attached thereto. A semi-circular pin receiving space or slot 154 is defined between the circular cap 52 and the distal end 150 of the plunger 134. A flange 156 extends into the semi-circular pin receiving space 154 to provide increased stability between the circular cap 152 and the distal end 150 of the plunger 134.

The two-way check valve 18 includes a second inlet 158 having a female luer connector 160 extends from the two-way check valve 160. The two-way check valve functions to permit fluid to flow in the inlet 28 and out the second inlet 158 under the influence of a negative pressure at the second inlet 158. Upon the application of a positive pressure at the second inlet 158, a check valve blocks the flow of fluid out of the inlet 28 and fluid is caused to flow out the outlet 32. The two-way check valve is described in detail in Mittleman, U.S. Pat. No. 4,084,606, which is incorporated by reference herein.

A preferred form of the elastomeric ambulatory infusion pump 20 is described in detail in Hessle, U.S. Pat. No. 4,769,008 and sold by Baxter Healthcare Corporation under the Intermate ® trademark. Briefly, the elastomeric ambulatory infusion pump 20 includes an elastomeric bladder 170 inside a protective housing 172. The inlet 34 of the elastomeric ambulatory infusion pump 20 has a luer connector 172. The elastomeric ambulatory infusion pump 20 further includes an outlet tube 176 connected to a flow regulator 178 in a manner described in detail in the Hessle patent. Prior to filling of the elastomeric bladder 170 with therapeutic fluid, the bladder is in a collapsed position about the mandrel 179. Injection of therapeutic fluid into the inlet 34 causes elastomeric bladder 170 to expand. As therapeutic fluid is injected into the elastomeric bladder 170, elastomeric tension of the bladder on the therapeutic fluid opposes injection of fluid, making it rather difficult to fill the elastomeric bladder 170. Once a selected amount of therapeutic fluid is injected into the elastomeric bladder 170, the second PVC tubing 130 can be disconnected from the luer connector 172 and the outlet tube 176 can be connected to a cannula or hypodermic needle (not shown) for intravascular injection of the therapeutic fluid at a controlled rate into a patient under the pressure created on the therapeutic fluid by the elastomeric bladder 170.

The syringe 16 is fit into the syringe driving apparatus 12 by moving the lever 176 to a fully opened position wherein the bumpers 96,100 rest upon the top 102 of the pedestal 74. The semi-circular pin receiving space 154 is then fit over the first and second pivot pins 108,110 in the manner illustrated in FIGS. 1 and 4. With the semi-circular pin receiving space over the first and second pivot pins 108,110, the flange 156 rests in the space between the first and second pivot pins 108,110. The cylinder 130 is then drawn forward relative to the plunger 134 until the point that the annular recess 148 of the port 140 of the syringe 16 can be received within the annular tongue 64. The cylinder is then rotated so that the indicia 135 faces upward.

Pivoting of the lever 76 forward and rearward in the manner illustrated by the arrow 180 in FIG. 8 causes the plunger 134 to move forward and rearward relative to the cylinder 130, as illustrated by the arrow 182. As the lever 76 is pivoted forward and rearward, the semi-circular pin receiving space 154 pivots over the first and second pivot pins 108,110. In addition, the cylinder 130 pivots about the first and second hinge pins 50,52 of the plate 48, as illustrated by the arrow 184. In this manner, the lever 76 may be pivoted forward and rearward thus causing insertion and withdrawal of the plunger 134 without imparting any torque on the distal end 150 of the plunger 134 or the port 140 of the cylinder 130. Also, as is readily apparent from FIGS. 1 and 8, the cylinder 130 of the syringe 16 is fixed against lengthwise movement relative to the base 36 of the syringe driving apparatus 12 by cooperation between the annular shoulder 144 and the annular collar 146 defining the annular recess 148 and the annular tongue 64. As the lever is pivoted forward, the circular cap 152 of the plunger 134 is received within the arcuate groove 112 of the bridge 84, thus preventing the circular cap 152 from striking the bridge 84. Moreover, once the circular cap 152 is received in the arcuate groove, the bridge 84 prevents disengagement of the pin receiving slot 154 from the hinge pins 108,110 until the lever is pivoted into the loading position illustrated in FIG. 1. It should also be appreciated that the bar 88 provides a significant mechanical advantage to an operator of the syringe driving apparatus who is pivoting the lever 76 forward and rearward by grasping the grip 90.

The fluid transfer apparatus 10 is assembled by loading of the syringe 16 into the syringe driving apparatus 12 in the manner set forth above. The lever 76 is then pivoted forward to expel all air out of the graduated cylinder 130. The male luer connector 142 of the port 140 of the syringe 16 is connected to the female luer connector 160 of the second inlet 158. Next, the vented spike 22 at the distal end of the first piece of PVC tubing 26 connected to the inlet 28 of the two-way check valve 18 is driven into the portal 24 of the therapeutic fluid supply 14. The lever 76 is then pivoted rearwardly by grasping the handle 90. First air trapped in the first piece of PVC tubing 26 and then therapeutic fluid is drawn into the cylinder 130 as the piston 132 is withdrawn. The air can then be vented through the second piece of PVC tubing 30 connected to the outlet port 32 of the two-way check valve 18 by pivoting the lever 76 forward by the handle 90. Following venting of the air from the system through the distal end of the second piece of PVC tubing 30, the distal end of the second piece of PVC tubing is connected to the luer connector 174 at the inlet 34 of the elastomeric ambulatory infusion pump 20 by means of a complementary luer connector (not shown) at the distal end of the second piece of PVC tubing 30. Following this connection, a selected volume of fluid is drawn into the cylinder 130 by again pivoting the lever 76 rearward by means of the handle 90. This selected volume can then be discharged from the cylinder 130 and into the elastomeric bladder 170 of the elastomeric ambulatory infusion pump 20. If a volume in excess of the volume of the cylinder 130 is desired to be injected into the elastomeric bladder 170, the lever 76 can be repeatedly pivoted rearward and forward until the desired volume of fluid has been injected into the elastomeric bladder 170.

Figure 3:
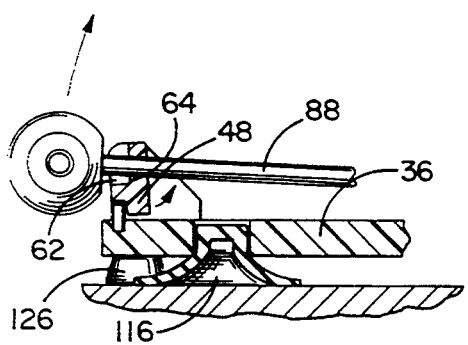
FIG. 3 is a cross-sectional view of the syringe driving apparatus of FIG. 1 taken along line 3—3 of FIG. 1.

Following use of the fluid transfer apparatus 10 in the manner set forth above, the fluid transfer apparatus 10 can be disassembled by retracing the steps discussed above. Following removal of the syringe 16 from the syringe driving apparatus 12, the syringe driving apparatus 12 can be placed into a compact configuration by pivoting the lever 76 fully forward so it attains the position illustrated in FIG. 2. As seen in FIG. 3, with the lever 76 pivoted fully forward, the bar 88 is received within the annular tongue 64 of the stepped arcuate groove 62 of the plate 48.

The fluid transfer apparatus of the present invention provides a mechanism for quickly and easily filling an elastomeric bladder of an elastomeric ambulatory infusion pump with a select volume of therapeutic fluid. The syringe driving apparatus of the present invention provides a lightweight and compact device for driving a piston forward and rearguard within a syringe with greater ease than manually operating the syringe. A syringe may be quickly and easily loaded into the syringe driving apparatus. Following use of the syringe driving apparatus, it is foldable into a compact configuration for convenient transport and easy storage. The syringe driving apparatus has a minimal number of mechanical linkages, providing a durable and reliable apparatus that can be assembled inexpensively. The suction cups on the base of the syringe driving apparatus permit the apparatus to be quickly secured to a non-porous surface of a fixture and the silicone bearings provide lateral stabilization as the lever is moved rearward and forward filling and exhausting a syringe. The pivoting connection for the cylinder of a syringe and the pivoting connection for the plunger of a syringe reduce stress on the syringe components, resulting in improved and extended syringe performance.

We claim:

1. An apparatus for driving a syringe, the syringe having an elongate cylinder with a fluid port at a first end of the cylinder and an open second end of the cylinder, a piston riding within the cylinder and a plunger having a proximal end connected to the piston and a distal end extending rearwardly from the open second end of the cylinder, the apparatus comprising:

a frame having a top and a bottom;

cylinder engaging means on top of the frame for engaging a cylinder of a syringe by movement of the cylinder in a first direction transverse the length of the cylinder to secure the cylinder without fasteners against lengthwise movement relative to the frame, and for disengaging the cylinder by movement of the cylinder in a second direction opposite the first direction;

a lever including first and second parallel spaced legs joined together by a transverse bridge, the lever being attached to the frame a selected distance from the cylinder engaging means for pivotable movement about a first axis; and plunger engaging means between the first and second legs proximate to but spaced from the bridge for engaging a distal end of a plunger of a syringe by movement of the plunger in the first direction in a pivotable connection about a second axis between the distal end of the plunger and the lever without fasteners and for disengaging the distal end of the plunger by movement of the plunger in the second direction.

2. The driving apparatus of claim 1 wherein the syringe further includes a nozzle extending forward from the fluid port of the cylinder of the syringe, and the cylinder engaging means comprises:

a plate on the frame fixed against lengthwise movement relative to the frame; and an arcuate tongue on the plate for receiving the nozzle by movement of the cylinder in the first direction.

3. The driving apparatus of claim 2 wherein the plate is pivotable about a third axis parallel to the first axis and the second axis.

4. The driving apparatus of claim 1 further comprising means for attaching the frame to a fixture to prevent sliding movement of the frame relative to the fixture.

5. The driving apparatus of claim 4 wherein the frame attaching means comprises at least one suction cup on the bottom of the frame.

6. The driving apparatus of claim 1 further comprising means for laterally stabilizing the frame.

7. The driving apparatus of claim 6 wherein the lateral stabilizing means comprises a plurality of spaced bumpers on the bottom of the frame.

8. The driving apparatus of claim 1 wherein the lever further comprises a handle extending lengthwise from the bridge oppositely of the first and second legs, whereby the handle provides a mechanical advantage decreasing the amount of force necessary to drive a plunger of a syringe forward and rearward within a cylinder.

9. The driving apparatus of claim 1 wherein the cylinder engaging means is configured to receive the lever when the lever is pivoted onto the top of the frame without a syringe attached to the frame for compact transport and storage of the riving apparatus.

10. The driving apparatus of claim 8 wherein the securing means comprises a plate pivotably attached to the top of the frame, the plate being fixed against lengthwise movement relative to the cylinder and pivotable about a third axis parallel to the first axis and the second axis, the plate further having a top edge defining an arcuate tongue for receiving the cylinder, the arcuate tongue further being configured for receiving the lever handle, whereby when a syringe is not attached to the driving apparatus the lever can be pivoted onto the top of the frame with the lever handle received in the arcuate tongue for compact storage of the driving apparatus.

11. The driving apparatus of claim 1 further comprising a block attached to the top of the frame, the lever pivotably attached to the block and a bumper on the lever for engaging the block to halt pivoting of the lever away from the top of the frame in a loading position.

12. The driving apparatus of claim 11 wherein the plunger has a pin receiving slot at its distal end, the slot being transverse to the length of the plunger, the plunger receiving means comprising a pin extending between the legs, the pin being spaced from the bridge such that with the cylinder secured by the securing means, the slot may clear the bridge to engage or disengage the pin only with the lever pivoted away from the frame top in a loading position.

13. The driving apparatus of claim 1 wherein the plunger engaging means comprises a pin attached to one of the legs extending transversely between the legs.

14. An apparatus for transferring a measured amount of fluid from a first fluid supply to a fluid reservoir, the apparatus comprising:
a syringe having an elongate cylinder with a front wall and rear opening, the syringe further including a piston riding within the cylinder and a plunger having a proximal end attached to the piston and a distal end extending rearwardly of the cylinder through the rear opening, there being a transverse slot in the plunger proximate the distal end, the cylinder further including a fluid port at the front wall, whereby as the piston is urged forward and rearward selected volumes are defined forward of the piston within the cylinder;
a frame;
cooperating means for engaging the cylinder to the frame by movement of the cylinder relative to the frame in a first direction transverse the length of the cylinder to secure the cylinder against lengthwise movement relative to the frame and for disengaging the cylinder by movement of the cylinder in a second direction opposite the first direction;
a lever having first and second parallel spaced legs joined together at their first ends by a transverse bridge, the lever being pivotable attached to the frame at their second ends a selected distance from the first cooperating means for pivotable movement about a first axis between a discharged position with the lever overlying the frame and a loading position with the lever pivoted away from the frame; and
a pin connected to one of the first and second legs proximate but spaced from the bridge, the pin extending substantially parallel to the first axis toward the other leg, the pin, with the lever in the loading position, being configured to receive the transverse slot in the distal end of the plunger of the syringe by movement of the plunger in the first direction for making a pivotable connection about a second axis between the end of the plunger and the lever.

15. The apparatus for transferring a measured amount of fluid of claim 15 further comprising a two-way check valve between the port, the fluid supply and the fluid reservoir, the two-way check valve permitting a flow of fluid a) from the fluid supply through the port and into the cylinder as the lever is moved from the discharged position toward the loading position and b) from the cylinder and into the fluid reservoir as the lever moves from the loading position toward the discharged position.

16. The apparatus for transferring a measured amount of fluid of claim 15 wherein the fluid reservoir is an elastomeric ambulatory infusion pump.

17. The apparatus for transferring a measured amount of fluid of claim 14 further comprising means on the frame for releasably attaching the frame to a fixture to prevent relative movement between the frame and the fixture.

18. The apparatus of claim 14 wherein when the lever is pivoted from the loading position the bridge prevents movement of the plunger in the second direction.

19. The apparatus of claim 14 wherein the fluid port of the syringe comprises a forwardly extending nozzle and the cooperating means comprises:
a plate fixed against lengthwise movement relative to the frame; and
an arcuate tongue on the plate for receiving the nozzle by movement of the cylinder in the first direction.

20. The apparatus of claim 19 wherein the plate is pivotably attached to the frame about a third axis parallel to the first and second axis, the plate further having a top edge defining the arcuate tongue.

21. The apparatus of claim 19 wherein the arcuate tongue receives the lever when the lever is pivoted into the discharged position and no syringe is engaged by the cooperating means.

22. A syringe driving system comprising:
a syringe, the syringe having an elongate cylinder with a fluid nozzle at a first of the cylinder and an open second end of the cylinder, a piston riding within the cylinder and a plunger having a proximal end connected to the piston and a distal end extending rearwardly from the open second end of the cylinder;
a frame having a top and a bottom;
means on top of the frame for engaging the nozzle of the cylinder by movement of the cylinder relative to the frame in a first direction transverse the length of the cylinder to secure the cylinder without fasteners against lengthwise movement relative to the frame, and for disengaging the cylinder by movement of the cylinder in a second direction opposite the first direction;

an elongate lever pivotably secured to the frame a selected distance from the plate, the selected distance being sufficient to receive lengthwise the cylinder of the syringe, the lever being pivotable about a first axis between a discharged position wherein the lever overlies the frame and a loading position wherein the lever is pivoted away from the frame; and plunger engaging means for pivotably engaging without fasteners the distal end of the plunger to the lever about a second axis parallel to the first axis at a location spaced from the first axis lengthwise of the lever by movement of the plunger in the first direction, whereby, upon attachment of the cylinder and plunger to the frame and the lever, pivotable movement of the lever is translated into movement of the plunger within the cylinder.

23. The syringe driving system of claim 22 wherein the plate is pivotable about a third axis parallel to the first axis of the lever.

24. The syringe driving system of claim 22 wherein the plunger engaging means comprises a pin extending from the lever along the second axis, the pin being receivable in a pin receiving slot at the distal end of the plunger of the syringe, the slot being transverse to the length of the plunger, the plunger being pivotable about the second axis as the lever is pivoted about the first axis.

25. The syringe driving system of claim 22 wherein the lever further comprises a handle extending lengthwise from beyond the attaching means, whereby the handle provides a mechanical advantage decreasing the amount of force necessary to drive the plunger of the syringe forward and rearward within the cylinder.

26. The syringe driving system of claim 22 wherein the nozzle engaging means of the plate receives the lever with the lever pivoted in the discharged position without syringe attached to the frame for compact transport and storage of the driving apparatus.

27. The syringe driving system of claim 25 wherein the plate has a top edge and the nozzle engaging means is an arcuate tongue for receiving an annular groove on the nozzle of the cylinder, the arcuate tongue further being configured for receiving the lever handle, whereby when a syringe is not attached to the driving apparatus the lever can be pivoted onto the discharged position with the lever handle received in the arcuate tongue for compact storage of the driving apparatus.

28. The syringe driving system of claim 22 wherein the lever further includes means for allowing the plunger to be moved in the first and second directions to engage or disengage the lever only with the lever in its loading position.

* * * * *

UNITED STATES PATENT AND TRADEMARK OFFICE
CERTIFICATE OF CORRECTION

PATENT NO. : 5,336,201
DATED : August 9, 1994
INVENTOR(S) : von der Decken

It is certified that error appears in the above-indentified patent and that said Letters Patent is hereby corrected as shown below:

Column 10, line 3, change "lever" to --legs--.

Column 10, line 3, change "pivotable" to --pivotably--.

Column 10, line 59, after "first" insert the word --end--.

Colume 12, line 13, insert "a" after --without--.

Signed and Sealed this

Seventeenth Day of January, 1995

*Attest:*

BRUCE LEHMAN

*Attesting Officer*     *Commissioner of Patents and Trademarks*